United States Patent [19]

Scholl et al.

[11] Patent Number: 4,923,952
[45] Date of Patent: May 8, 1990

[54] MONOFORMYLATED 3,3'-DIAMINODIPROPYLAMINES, A PROCESS FOR THEIR PRODUCTION AND THEIR USE

[75] Inventors: Hans-Joachim Scholl, Cologne; Helmut Reiff, Leverkusen, both of Fed. Rep. of Germany

[73] Assignee: Bayer Aktiengesellschaft, Leverkusen, Fed. Rep. of Germany

[21] Appl. No.: 329,472

[22] Filed: Mar. 28, 1989

[30] Foreign Application Priority Data

Apr. 2, 1988 [DE] Fed. Rep. of Germany ....... 3811342

[51] Int. Cl.$^5$ .............................................. C08G 18/38
[52] U.S. Cl. ........................................ 528/60; 528/61; 564/215
[58] Field of Search ...................... 528/60, 61; 564/215

[56] References Cited

U.S. PATENT DOCUMENTS 4,238,409 12/1980 Rigdon et al. ................. 260/501.17
4,348,536 9/1982 Blahak et al. ........................ 560/169
4,701,546 10/1987 Bewert et al. ....................... 558/445

FOREIGN PATENT DOCUMENTS 735771 6/1943 Fed. Rep. of Germany .

Primary Examiner—Maurice J. Welsh
Attorney, Agent, or Firm—Joseph C. Gil; Thomas W. Roy

[57] ABSTRACT

The present invention is directed to monoformylated 3,3'-diaminodipropylamine mixtures corresponding to formulae I and II

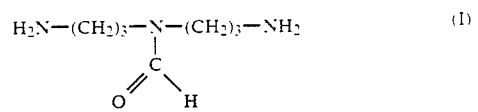

(I)

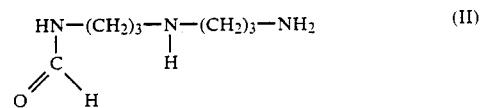

(II)

The present invention is also directed to a process for the production of these mixtures by reacting acrylonitrile and formamide in the presence of a 4-aminopyridine derivative to form N,N-bis-(2-cyanoethyl)-formamide which is then hydrogenated to the monoformylated 3,3'-diaminopropylamine mixture corresponding to formulae I and II.

Finally, the present invention is also directed to the use of these mixtures as chain extending agents for the preparation of polyurethanes by the polyisocyanate polyaddition process.

7 Claims, No Drawings

MONOFORMYLATED 3,3'-DIAMINODIPROPYLAMINES, A PROCESS FOR THEIR PRODUCTION AND THEIR USE

BACKGROUND OF THE INVENTION

1. Field of the Invention

This invention relates to new monoformylated 3,3'-diaminodipropylamines or mixtures thereof, to a process for their production from acrylonitrile/formamide with subsequent hydrogenation and to their use as chain-extending agents in the production of polyurethanes by the isocyanate polyaddition process.

DESCRIPTION OF THE PRIOR ART

Reactions of acrylonitrile and formamide in the presence of bases have been described. Thus, according to DRP 735,771, N,N-bis-(2-cyanoethyl)-formamide is obtained from 2 moles of acrylonitrile and 1 mole of formamide using catalytic quantities of sodium.

The drastic production methods disclosed can be expected to produce considerable amounts of impurities, for example by further reaction of N,N-bis-(2-cyanoethyl)-formamide with acrylonitrile, which prevent preparation of diamine mixtures I and II according to the invention in pure form.

DE-OS No. 3,520,982 describes the reaction of acrylonitrile with formamide in the presence of a tertiary amine base to form 2-(N-formylamino)-propionitrile. According to the data provided, selectivity and yield are both high. However, the bisadduct, N,N-bis-(2-cyanoethyl)-formamide, was not found.

Accordingly, it must be regarded as extremely surprising that N,N-bis-(2-cyanoethyl)-formamide is formed at all, let alone in high yields, good selectivity and purity, by the process according to the invention.

SUMMARY OF THE INVENTION

The present invention is directed to monoformylated 3,3'-diaminodipropylamine mixtures corresponding to formulae I and II

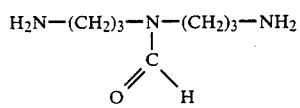

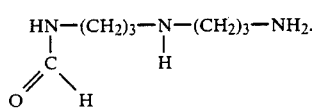

The present invention is also directed to a process the production of these mixtures by reacting acrylonitrile and formamide in the presence of a 4-aminopyridine derivative to form N,N-bis-(2-cyanoethyl)-formamide which is then hydrogenated to the monoformylated 3,3'-diaminopropylamine mixture corresponding to formulae I and II.

Finally, the present invention is also directed to the use of these mixtures as chain extending agents for the preparation of polyurethanes by the polyisocyanate polyaddition process.

DETAILED DESCRIPTION OF THE INVENTION

The formamide may be used in a quantity of about 0.5 to moles, preferably about 0.5 to 2 moles, per mole acrylonitrile.

Suitable 4-aminopyridine derivatives include those corresponding to formula (III)

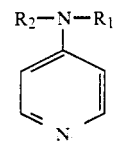

wherein $R_1$ and $R_2$ may be the same or different and represent a $C_1-C_6$ alkyl radical or $R_1$ and $R_2$ together represent a $C_3-C_5$ alkylene radical. N,N-dimethyl-4-aminopyridine or 4-pyrrolidinopyridine is preferably used.

The quantity in which this catalytically active base is used is not critical. To obtain a sufficiently rapid conversion, it is normally used in a quantity of about 0.5 to 10 mole-% per mole acrylonitrile. Acrylonitrile is used in its commercial form in which it contains small quantities of standard polymerization inhibitors.

The process may be carried out in the absence of a solvent, but a solvent is preferably used. To increase selectivity, increasing quantities of solvent have to be added at increasing reaction temperatures. Suitable solvents include polar solvents such as tetrahydrofuran, dimethyl acetamide or acetonitrile. Acetonitrile is particularly preferred.

Suitable reaction temperatures include temperatures of about 0° to 120° C., preferably about 20° to 100° C. The solvent-free embodiment of the process is preferably being carried out at room temperature. The process is preferably carried out at normal pressure, although it may be carried out under elevated pressure.

The process according to the invention does not require any special process measures. The same applies to the purification step. After separation of the low-boiling constituents, formamide and the catalyst (for example by distillation or thin-layer evaporation), N,N-bis-(2-cyanoethyl)-formamide is obtained in the form of a faintly colored liquid which is of standard intermediate-product purity. There is no need for further purification steps because the prohibitive impurities of the prior art are not formed in the process according to the invention.

The next step of the process according to the invention comprises the known hydrogenation of the two nitrile groups of N,N-bis-(2-cyanoethyl)-formamide. The process may be conducted in methanol/ammonia as solvent using Raney nickel/iron as the hydrogenation catalyst at temperatures of about 20° to 60° C. and under a hydrogen pressure of about 20 to 50 bar. After separation of the catalyst and low-boiling constituents (ammonia/methanol), the monoformulated 3,3'-diaminopropylamine mixtures of formulae I and II according to the invention may be directly obtained in excellent quality.

The crucial point of the invention is that the process according to the invention for the production of N,N-bis-(2-cyanoethyl)-formamide for the first time provides a sufficiently pure starting product which enables the monoformylated diamines I and II according to the invention to be readily produced in high quality by known hydrogenation methods.

The monoformylated 3,3'-diaminodipropylamine mixture according to the invention is a low viscosity liquid at room temperature with no tendency to crystallize. Its odor is only faintly aminic.

The monoformylated 3,3'-diaminodipropylamine mixture according to the invention is a new, special chain-extending agent for the production of polyisocyanate polyaddition products, preferably polyurethane plastics by the isocyanate polyaddition process. Chain extension may first be effected through the two amino groups and may optionally be followed by further reactions of the

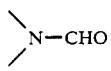

function. Possible reactions include oxidation, reduction or hydrolytic and/or thermal decomposition.

The diamine mixture according to the invention may be used, for example, for the synthesis of dissolved polyurethane polyureas by the solution polyaddition process. In this synthesis an NCO prepolymer containing about 0.5 to 10% by weight NCO is dissolved in a solution and the resulting solution is chain extended in steps with the diamine mixture according to the invention until viscosity of about 5000 to about 70,000 mPa.s is obtained. The solids content is normally between about 20 and 40% by weight. It is also possible to initially introduce the diamine mixture according to the invention and then carry out the polyaddition by addition of the NCO prepolymer solution.

The solvents used are known and include dimethylformamide, dimethylacetamide, N-methyl-pyrrolidone or mixtures of aromatics and alcohols such as toluene/isopropanol.

The final properties of the polyurethane ureas may be specifically established, for example, by using certain monoamines (partial chain termination, viscosity reduction), diamines typically used in PUR chemistry, optionally containing salt groups (carboxyl or sulfonate groups), or triamines (branching, viscosity increase, crosslinking) in addition to the diamine mixture according to the invention.

In addition, the diamine mixture according to the invention may be used with particular advantage instead of conventional diamines for the production of aqueous polyurethane dispersions of the type described, for example, in Angew Makromol. Chemie 26, 1972, 85–106. In this embodiment an additional reaction may also optionally be carried out with the

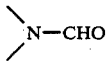

group.

The diamine mixture according to the invention may also be used as an aminic hardener for epoxies. For example, the hardener used in typical two-component epoxy adhesives may be replaced by the diamine mixture according to the invention. In this embodiment colorless, elastic and very firmly adhering adhesives are formed.

The invention is illustrated by the following examples, in which all percentages are percentages by weight.

EXAMPLES

EXAMPLE 1

Preparation of N,N'-bis-(2-cyanoethyl)-formamide 14.7 g N,N-dimethyl-4-aminopyridine were introduced with stirring at room temperature into a solution of 212 g acrylonitrile, 212 g acetonitrile and 180 g formamide. The clear solution was refluxed for 21 hours; the internal temperature rose from 86° C. to about 92° C.

The reaction solution was then freed from low-boiling constituents (30°–40° C./1 to 20 mbar) and the light yellow, clear crude solution was separated off in a thin-layer evaporator (145° C/0.1 mbar) from residual, relatively low-boiling constituents. 99% of a light yellow, clear liquid was obtained which consisted of N,N'-bis-(2-cyanoethyl)-formamide (GC).

Yield: 170 g, conversion: 59% (based on acrylonitrile), selectivity: 95%.

| Analysis (%): | C | H | N |
|---|---|---|---|
| Found: | 55.3 | 6.3 | 27.8 |
| Calculated: (based on $C_7H_9N_3O$) | 55.6 | 6.0 | 27.8 |

EXAMPLE 2

Preparation of N,N'-bis-(2-cyanoethyl)-formamide 27.5 g N,N'-dimethyl-4-aminopyridine were introduced with stirring at room temperature into a solution of 770 g acrylonitrile and 433 g formamide. The clear solution was left standing for 4 days at room temperature. The reaction solution was freed from low-boiling constituents (room temperature/1 to 20 mbar) and residual low-boiling constituents were separated off in a thin-layer evaporator (145° C./0.1 mbar). The sump liquid obtained was substantially colorless and clear.

Yield: 621 g N,N'-bis-(2-cyanoethyl)-formamide.
Purity: 98% (GC).
Conversion: 53% (based on acrylonitrile).
Selectivity: 96%.

EXAMPLE 3

Preparation of the monoformylated 3,3'-diaminodipropylamine mixtures of formulae I and II 1000 ml methanol, 500 ml ammonia and 40 g Raney nickel/iron (Ni:Fe ratio: 85:15) were added to 255 g N,N'-bis(2-cyanoethyl)-formamide from Example 2 in a stirred autoclave. The mixture was then stirred at 30° C./30–50 bar hydrogen pressure until the uptake of hydrogen stopped. The autoclave was then vented, the catalyst was filtered off and the low-boiling constituents (ammonia and methanol) were separated. 262 g (98% yield) of an almost colorless, clear, low viscosity liquid amine mixture corresponding to formulae I and II was obtained in which the molar ratio of products was approximately 50:50 according to $1^H$-NMR investigations.

| Analysis (%) | C | H | N |
|---|---|---|---|
| Found: | 53.0 | 10.5 | 26.4 |

| Analysis (%) | C | H | N |
|---|---|---|---|
| Calculated: (based on C₇H₁₇N₃O) | 52.8 | 10.7 | 26.4 |

The base nitrogen content amounted to 17.4% (theoretical 17.6%).

EXAMPLE 4

Comparison with Example 3

Luprintan PFD (a product of BASF), a commercial form of N,N'-(2-cyanoethyl)-formamide was tested for comparison.

255 g Luprintan PFD were hydrogenated as in Example 3. 237 g (88% yield) of a dark-colored, thick, liquid amine mixture containing 15.2% nitrogen (theoretical 17.6%) was obtained.

| Analysis (%) | C | H | N |
|---|---|---|---|
| Found: | 51.8 | 9.9 | 25.6 |
| Calculated: (based on C₇H₁₇N₃O) | 52.8 | 10.7 | 26.4 |

The above data demonstrates that this product was of comparatively poor quality.

The following examples demonstrate possible uses of the monoformylated amine mixtures (I) and (II) according to the invention.

NCO prepolymer 1:

830.5 g (0.489 mole) of a polyester of adipic acid, hexane-1,6-diol and neopentyl glycol (molar ratio of glycols 65:35) having a molecular weight of 1700 and 28.3 g (0.013 mole) of a monofunctional, n-butanol-started ethylene oxide/propylene oxide polyether (molar ratio EO:PO 83:17) having a molecular weight of 2150 were dehydrated in vacuo for 30 minutes at 110° C. After cooling to 55°-60° C., a mixture of 122 g (0.55 mole) 1-isocyanatomethyl-5-isocyanato-1,3,3-trimethyl-cyclohexane and 92.5 g (0.55 mole) 1,6-diisocyanatohexane was added. After 15 minutes, the mixture was heated to 120° C. and stirred at that temperature for 2 hours. The mixture was then dissolved in 340 ml acetone to a solids content of 80%. The solution had an NCO content of 3.3% (theoretical 3.7%).

NCO prepolymer 2:

403.7 g (0.238 mole) of the polyester from NCO prepolymer 1 were dehydrated for 30 minutes in a water jet vacuum at 110° C. After cooling to 60°-70° C., 96.3 g (0.434 mole) 1-isocyanatomethyl-5-isocyanato-1,3,3-trimethylcyclohexane were added and the mixture was heated for about 15 minutes to 100° C. After 1.5 h, the mixture was dissolved in toluene to form a 70% solution which had an NCO content of 1.8% (theoretical 2.3%).

APPLICATION EXAMPLES (A) Polyurethane Ureas By Solution Polyaddition (A1) 100 g prepolymer solution 2 were slowly added dropwise in portions to a solution of 3.81 g (23.7 mmole) of the diamine mixture of Example 3 according to the invention and 1.6 g (5.4 mmole) octadecyl isocyanate in a mixture of 80 g toluene, 80 g isopropanol and 32 g ethylene glycol monoethyl ether. A pale yellow, clear solution having a solids content of 25.5% and a viscosity (23° C) of 7500 mPa.s was obtained.

Glass plates and aluminum foils were coated with the solution and the solvent evaporated at 130° C. An optically clear, soft but tack-free coating was obtained. The polyurethane urea film was highly elastic and possessed excellent adhesion to aluminum.

(A2) A mixture of 100 g prepolymer solution 2 and 1.8 g octadecyl isocyanate was added dropwise over a period of 2 hours at 50° C. to a solution of 3.81 g (0.024 mole) of the amine mixture of Example 3 according to the invention in 192 g N,N-dimethylformamide. After cooling to room temperature, a light yellow, clear solution having a solids content of 25% and a viscosity of 11,000 mPa.s was obtained. The film produced at 130° C. was colorless and clear.

(A3) The procedure was exactly the same as in (A2), except that the amine mixture of Example 4 was used. The polymer solution obtained was brown and slightly opaque with a viscosity of only 1000 mPa.s. The corresponding film was also brown and slightly opaque.

(B) PREPARATION OF POLYURETHANE UREA DISPERSIONS IN WATER (B1) 250 g prepolymer solution 1 were diluted with 450 ml acetone to a solids content of 33%. A mixture of 4.15 g (0.011 mole) of a 50% aqueous solution of the sodium salt of 2-aminoethyl-β-aminoethane sulfonic acid, 0.71 g (0.014 mole) hydrazine hydrate and 6.8 g (0.04 mole) of the amine mixture of Example 3 according to the invention in 50 ml deionized water was added to the diluted solution of prepolymer solution 1 at 50 to 55° C. After 15 minutes, the product was dispersed over a period of 6 minutes in 440 ml deionized water. After removal of the acetone by distillation in a water jet vacuum, a finely divided dispersion having a solids content of 33.8% was obtained. The film produced at 120° C. was optically clear and colorless.

(B2) The procedure was exactly the same as in Example (B1) except that 6.8 g (0.04 mole) of the amine Comparison Example 4 was used instead of the amine produced in accordance with Example 3. The dispersion obtained was finely divided, but produced some dark-brown sediment after standing overnight.

(B3) For further comparison with Example B1, Example B1 was again repeated with the exception that 7.22 g (0.043 mole) 1-aminomethyl-5-amino-1,3,3-trimethylcyclohexane (isophorone diamine) were used instead of the amine mixture according to the invention. A coarse-particle dispersion having a solids content 34% was obtained. The film produced at 120° C. was opaque in appearance which is indicative of inhomogeneities.

The following data were determined for dispersions B1 to B3:

| | B1 | B2 (Comp) | B3 (Comp) |
|---|---|---|---|
| Solids Content | 33.8% | 34.2% | 34.0% |
| pH value | 7-8 | 7-8 | 7-8 |
| Sulfonate content | 0.42% | 0.42% | 0.42% |
| Particle size (nm) | 95 | 240 | 220,800 |
| Distribution | narrow, monomodal | some brown sediment | modal |

(C) Use Of The Diamine Mixture According To The Invention As A Hardener For Epoxy Resins 1 g of a commercial epoxy resin (Uhu 300 Binder, a product of the Uhu company, D 7580, Bühl) was thoroughly mixed with 0.34 g of the diamine mixture of Example 3 according to the invention. The product hardened after 10 minutes at 100° C. The film of the two-component adhesive was scratch-resistant, colorless and optically clear.

When the test was repeated using 0.35 g of the diamine mixture of Comparison Example 4, the film obtained was yellow-brown rather than colorless, but otherwise the same.

When films were hardened overnight at room temperature, the results were identical.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A monoformylated 3,3'-diaminodipropylamine mixture corresponding to formulae I and II in a ratio of 1:99 to 99:1 mole-%.

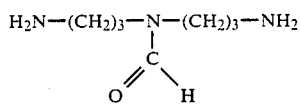

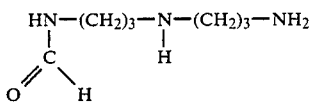

2. The mixture of claim 1 wherein the compounds of formulae I and II are present in a ratio of 20:80 to 80:20 mole-%.

3. A process for the production of a monoformylated 3,3'-diaminodipropylamine mixture corresponding to formulae I and II

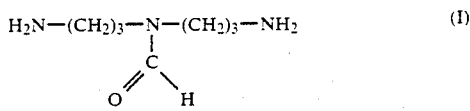

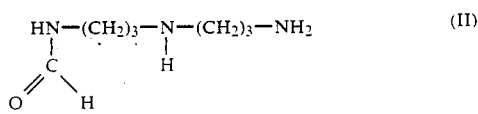

which comprises reacting acylonitrile and formamide in the presence of a 4-aminopyridine derivative to form an N,N'-bis-(2-cyanoethyl)-formamide intermediate and subsequently hydrogenating said intermediate.

4. The process of claim 3 wherein said 4-aminopyridine derivative corresponds to the formula

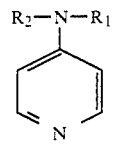

wherein $R_1$ and $R_2$ may be the same or different and represent a $C_1$-$C_6$ alkyl radical or $R_1$ and $R_2$ together represent a $C_3$-$C_5$ alkylene radical.

5. The process of claim 3 wherein said 4-aminopyridine derivative is used in a quantity of about 0.5 to 10 mole-%, based on acrylonitrile.

6. The process of claim 4 wherein said 4-aminopyridine derivative is used in a quantity of about 0.5 to 10 mole-%, based on acrylonitrile.

7. A polyurethane prepared by reacting an isocyanate-terminated prepolymer with the chain extender mixture of claim 1.

* * * * *